United States Patent [19]
Merz et al.

[11] 4,087,532
[45] * May 2, 1978

[54] ANALGESICALLY USEFUL 2-TETRAHYDROFURFURYL-5-LOWER ALKYL-2-OXY-6,7-BENZOMORPHANS AND SALTS THEREOF

[75] Inventors: Herbert Merz; Adolf Langbein, both of Ingelheim am Rhein; Gerhard Walther; Klaus Stockhaus, both of Bingen am Rhein, all of Germany

[73] Assignee: Boehringer Ingelheim GmbH, Ingelheim am Rhein, Germany

[*] Notice: The portion of the term of this patent subsequent to Sep. 21, 1993, has been disclaimed.

[21] Appl. No.: 673,116

[22] Filed: Apr. 2, 1976

Related U.S. Application Data

[63] Continuation of Ser. No. 555,350, Mar. 5, 1975, abandoned.

[30] Foreign Application Priority Data

Mar. 9, 1974 Germany .............................. 2411382
Mar. 9, 1974 Germany .............................. 2411382

[51] Int. Cl.² ................. C07D 221/26; A61K 31/445
[52] U.S. Cl. ............................ 424/267; 260/293.54; 260/293.67; 260/DIG. 13
[58] Field of Search .................... 260/293.54; 424/267

[56] References Cited

U.S. PATENT DOCUMENTS

| 3,499,906 | 3/1970 | Robinson et al. | 260/293.4 |
| 3,647,806 | 3/1972 | Cross | 260/293.54 |
| 3,823,150 | 7/1974 | Merz, et al. | 260/293.54 |
| 3,982,005 | 9/1976 | Merz et al. | 260/293.54 |

Primary Examiner—Henry R. Jiles
Assistant Examiner—Richard A. Schwartz
Attorney, Agent, or Firm—Hammond & Littell

[57] ABSTRACT

Compounds of the formula

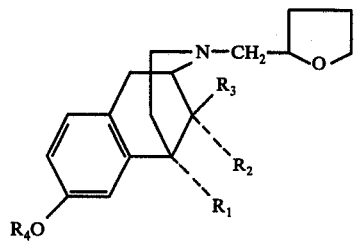

wherein
$R_1$ is methyl, ethyl or propyl,
$R_2$ is hydrogen, methyl or ethyl,
$R_3$ is hydrogen or methyl, and
$R_4$ is hydrogen, alkyl of 1 to 4 carbon atoms or alkanoyl of 2 to 5 carbon atoms, and non-toxic, pharmacologically acceptable acid addition salts thereof; the compounds as well as the salts are useful as analgesics.

9 Claims, No Drawings

ANALGESICALLY USEFUL 2-TETRAHYDROFURFURYL-5-LOWER ALKYL-2-OXY-6,7-BENZOMORPHANS AND SALTS THEREOF

This is a continuation of copending application Ser. No. 555,350, filed Mar. 5, 1975, now abandoned.

This invention relates to novel 2-tetrahydrofurfuryl-5-lower alkyl-2'-oxy-6,7-benzomorphans and non-toxic acid addition salts thereof, as well as to various methods of preparing these compounds.

More particularly, the present invention relates to a novel class of compounds represented by the formula

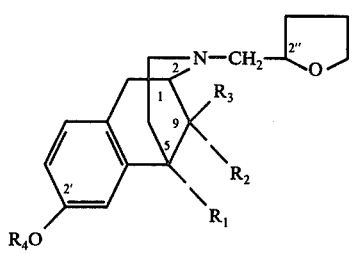

wherein
$R_1$ is methyl, ethyl or propyl,
$R_2$ is hydrogen, methyl or ethyl,
$R_3$ is hydrogen or methyl, and
$R_4$ is hydrogen, alkyl of 1 to 4 carbon atoms or alkanoyl of 2 to 5 carbon atoms,
and non-toxic, pharmacologically acceptable acid addition salts thereof.

In formula I above the broken lines indicate that substituents $R_1$ and $R_2$ are arranged in cis-configuration with respect to the carbocyclic ring, which means that when $R_1$ and $R_2$ are both alkyl and $R_2$ and $R_3$ are different, only compounds of the α-series with cis-positioned alkyl substituents $R_1$ and $R_2$ are embraced by the formula.

A preferred sub-genus is constituted by those compounds of the formula I wherein $R_4$ is hydrogen and the remaining substituents have the meaning previously defined. Especially preferred are those compounds of the formula I wherein $R_1$ and $R_2$ are methyl and $R_3$ and $R_4$ are hydrogen, that is, 2-tetrahydrofurfuryl-2'-hydroxy-5,9-dimethyl-6,7-benzomorphans.

In the light of the foregoing definition of the compounds embraced by formula I, the following situation results with respect to stereoisomerism: The norbenzomorphans from which the compounds of the present invention are derived, that is, the compounds of the formula

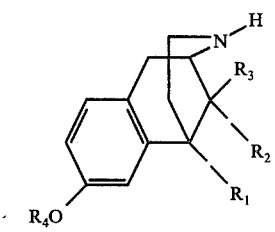

wherein $R_1$ through $R_4$ have the meanings defined in connection with formula I, comprise two centers of asymmetry when $R_2$ and $R_3$ are identical, and three centers of asymmetry when $R_2$ and $R_3$ are not identical. However, due to the rigid incorporation of the C-1 and C-5 centers of asymmetry into a bridged ring system and because of the fixed position of the C-9 center of asymmetry (limitation to the α-series) the nor-compounds of the formula II exist only in a single racemic form and as the corresponding optical antipodes, as follows:

| Designation | Form of II | Configuration |
|---|---|---|
| (±) - II | racemic | — |
| (−) - II | levo-rotatory | 1 R, 5 R, 9 R |
| (±) - II | dexgro-rotatory | 1 S, 5 S, 9 S |

The N-tetrahydrofurfuryl-substitution of the nor-compound introduces an additional center of asymmetry into the molecule (at C-2" in the tetrahydrofuran ring). Therefore, it is to be expected that formula I, as above defined, embraces two series (I, 1) and (I, 2) of racemic diastereoisomers and the corresponding optical antipodes, which owe their existence to the following possible combinations:

| Desig-nation | Configuration Benzomorphan moiety | N-tetrahydro-furfuryl group | |
|---|---|---|---|
| I,1 | 1 R, 5 R, 9 R-(−) | D-(−) | racemic diastereoisomer 1 |
|  | 1 S, 5 S, 9 S-(+) | L-(+) |  |
| I,2 | 1 R, 5 R, 9 R-(−) | L-(+) | racemic diastereoisomer 2 |
|  | 1 S, 5 S, 9 S-(+) | D-(−) |  |

Which of the optical antipodes belonging to (I,1) or (I,2), respectively, is the levo-rotatory form or the dextro-rotatory form can fundamentally not be determined solely on the basis of configuration, but can be ascertained only by measurement in a polarimeter.

In connection with some of the 2-tetrahydrofurfuryl-2'-hydroxy-5,9α-dimethyl-6,7-benzomorphans of this invention (e.g. formula I, $R_1=R_2=-CH_3$ and $R_3=R_4=H$) which we investigated, we found that the direction of optical rotation of the precursor of the formula II is not altered by the introduction of the D-(−)- or L-(+)-tetrahydrofurfuryl substituent. It is probably, but by no means predictable with certainty, that this situation also applies to compounds of the formula I with other combinations of substituents $R_1$ to $R_4$.

As far as the nomenclature of the compounds of the formula I is concerned, the naming of the optically active embodiments offers no difficulties, as can be seen from the above table. Thus, when the designation 1R, 5R, 9R or 1S, 5S, 9S is used, the configuration at C-9 is clearly established, so that the "α" can be omitted in the chemical nomenclature. On the other hand, in connection with the racemic compounds it is not possible to predict which of the two possible diastereoisomers is obtained; hence, in the following description of the present invention both racemic diastereoisomers are designated by (±) and differentiated from each other by the supplement "diastereoisomer 1" or "diastereoisomer 2", where 1 and 2 merely indicates the sequence in which they were isolated.

The compounds embraced by formula I, as above defined, may be prepared by a number of different methods among which the following have proved to be particularly convenient and efficient:

Method A

By alkylating a norbenzomorphan of the formula II above with a tetrahydrofurfuryl compound of the formula

(III)

wherein X is a nucleophylically exchangeable substituent, such as arylsulfonyloxy, aralkylsulfonyloxy, alkylsulfonyloxy or preferably halogen, especially chlorine, bromine or iodine.

The calculated quantity of the alkylating agent of the formula III or preferably an excess thereof is provided, and the reaction is advantageously performed in the presenceof an acid-binding agent, such as triethylamine, dicyclohexylethylamine, sodium carbonate, potassium carbonate, calcium oxide or preferably sodiumbicarbonate. Although it is not required to use a solvent, the preformance of the reaction in an inert solvent, such as chloroform, toluene, ethanol, nitromethane, tetrahydrofuran, dimethylsulfoxide or preferably dimethylformamide, is more advantageous. Mixtures of two or more of these solvents may also be used. Finally, an excess of the alkylating agent, for example an excess of tetrahydrofurfuryl bromide, may serve as the solvent as well. The reaction temperature is variable in wide limits, the lower limit being given by too slow a reaction rate, and the upper limit being given by an increased occurrence of side-reactions. Temperatures between 50° and 150° C, preferably 100° C, are acceptable. If the reaction is performed with a less reactive alkylating agent, such as with tetrahydrofurfuryl chloride, the reaction may be accelerated by addition of a catalytic or equimolar quantity of potassium iodide or sodium iodide.

METHOD B

By reducing a carbonamide or thioamide of the formula

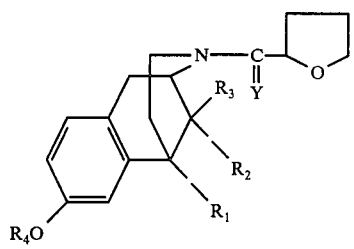

wherein $R_1$ through $R_4$ have the same meanings as in formula I and Y is oxygen or sulfur.

The reduction of a carbonamide of the formula IV (Y is oxygen) may be effected pursuant to various methods. Especially suitable is the reduction with a complex hydride of high reducing power, especially with lithium aluminum hydride. The hydride is provided in the calculated amount or in excess, preferably up to twice the calculated amount. The reaction is advantageously carried out in an inert solvent, preferably in diethyl ether, diisopropyl ether or especially tetrahydrofuran. The reaction temperature is variable within wide limits and lies advantageously between 0° C and the boiling point of the solvent.

During the reduction of an O-acyl derivative of a carbonamide of the formula IV ($R_4$ is alkanoyl and Y is oxygen) with a complex metal hydride, such as during the reduction with lithium aluminum hydride, not only the carbonyl group is reduced, but simultaneously also the O-acyl group is reductively split off, and in this case a compound of the formula I is obtained wherein $R_4$ is hydrogen.

The reduction of a thioamide of the formula IV (Y is sulfur) takes place much more easily than that of a carbonamide. It may be effected with a complex hydride or with nascent hydrogen (generated, for example, by zinc/hydrochloric acid, zinc/acetic acid or aluminum amalgam/water); it is also possible to desulfurize the thioamide with Raney nickel, or to effect the reduction electrochemically. By using a reducing agent with stronger reducing power, O-acyl groups may simultaneously be split off reductively. In this case a compound of the formula I wherein $R_4$ is hydrogen is obtained.

METHOD C

By reducing a compound of the formula

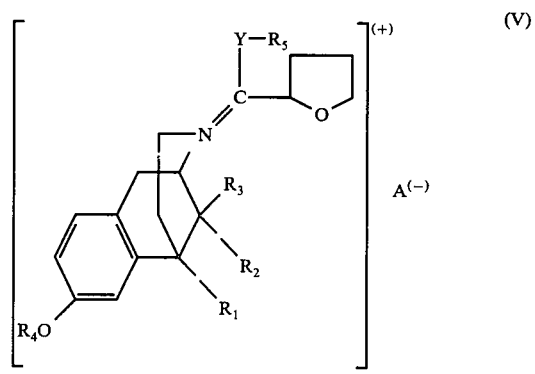
(V)

wherein $R_1$ through $R_4$ and Y have the meanings previously defined, $R_5$ is an alkyl group of up to 4 carbon atoms, preferably methyl, and $A^{(-)}$ the anion of an inorganic or organic acid.

The reduction may be effected pursuant to various methods, for example, by those indicated above under method B for the reduction of the thioamides; however, as the compounds of the formula V tend to decompose and undergo side-reactions (e.g. hydrolysis, aminolysis), a restriction has to be made. It has proved to be of advantage to continue reacting a compound of the formula V immediately without isolation. The use of a complex metal hydride with reduced reducing power, such as sodium borohydride, is of advantage. Furthermore, it is possible to effect reduction with nascent hydrogen or with hydrogen in the presence of a hydrogenation catalyst, such as Raney nickel. Depending upon the reaction conditions, O-acyl groups may simultaneously be split off in the course of the reduction.

METHOD D

By Hofmann's degradation of a quaternary ammonium compound of the formula

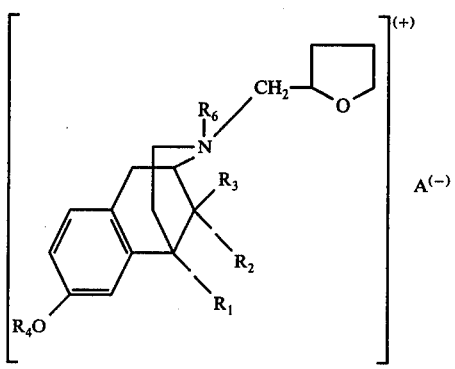

wherein $R_1$ through $R_4$ and $A^{(-)}$ have the meanings previously defined and $R_6$ is a group removable by the Hofmann Elimination, such as β-phenylethyl, naphthylethyl or 1,2-diphenylethyl.

The reaction is effected by the action of a base upon the quaternary salt and may be performed in various ways. Under the conditions of the Hofmann Elimination O-acyl groups may be split off, whereby a corresponding compound of the formula I is obtained, wherein $R_4$ is hydrogen.

METHOD E

By cylizing a compound of the formula

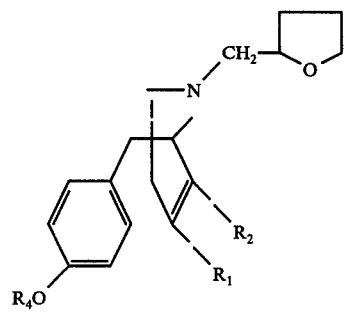

or

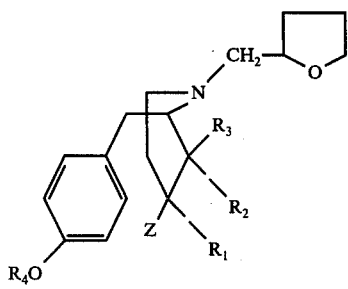

wherein $R_1$ through $R_4$ have the meanings previously defined and Z is halogen, hydroxyl, alkoxy, acyloxy, arylsulfonyloxy or alkylsulfonyloxy.

The cyclization reaction may be effected pursuant to known methods. For example, it is performed under the conditions of the Friedel-Crafts Reaction with aluminum chloride in carbon disulfide, or with a strong acid, such as phosphoric acid or polyphosphoric acid, preferably at temperatures between 100° and 150° C. Cyclization of a compound of the formula VIIa yields a compound of the formula I wherein $R_3$ is hydrogen. Under the cyclization reaction conditions O-acyl or O-alkyl groups may be split off, whereby a compound of the formula I with a free phenolic hydroxyl group ($R_4$ = hydrogen) is obtained.

METHOD F

By tetrahydrofuran ring closure of a compound of the formula

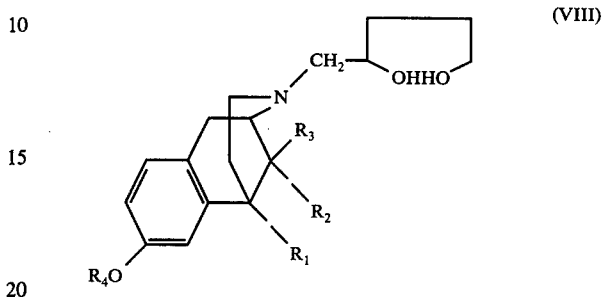

wherein $R_1$ through $R_4$ have the meanings previously defined.

In order to cyclize to tetrahydrofuran ring a variety of different methods may be applied. For example, the dehydration leading to cyclization may be brought about by the action of an acid catalyst upon a compound of the formula VIII. Suitable acid catalysts are, for example, inorganic or organic acids or acid salts, such a sulfuric acid, phosphoric acid, oxalic acid, p-toluenesulfonic acid, sodium bisulfate or anhydrous zinc chloride. The reaction is preferably carried out at elevated temperatures, most advantageously between 100° and 200° C. It is of advantage to remove the water which is split off with the aid of water-binding agents, such as an excess of sulfuric acid or zinc chloride, or by azeotropic distillation. Frequently, it is of advantage to replace one of the two hydroxyl groups intermediately by a more reactive group. Thus, for example, the cyclization may be effected with toluenesulfonic acid chloride in pyridine without isolating the o-toluenesulfonyloxy-derivative of the compound of the formula VIII which is intermediately formed. Depending upon the relative severity of the reaction conditions, O-acyl and O-alkyl groups may simultaneously be split into free phenolic hydroxyl groups.

METHOD G

A compound of the formula I wherein $R_4$ is hydrogen is obtainable by ester cleavage of a compound of the formula

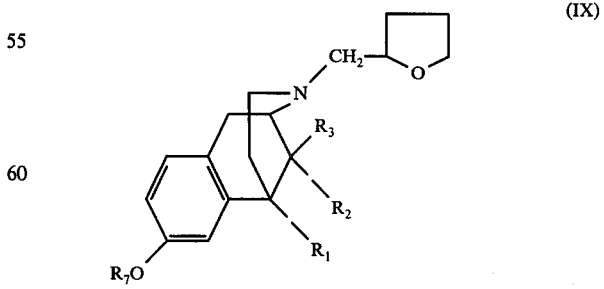

wherein $R_1$ through $R_3$ have the meanings previously defined and $R_7$ is an acyl group derived from an inorganic or organic acid. Examples of such acyl groups are, above all, lower aliphatic or simple aromatic and heterocyclic acyl groups, in particular acetyl, propionyl, benzoyl and tetrahydro-2-furoyl groups.

The cleavage may be effected by various methods. The most simple one is acid or alkaline hydrolysis, which is preferably carried out in aqueous, alcoholic or aqueous-alcoholic solution. The reaction temperature, which is variable within wide limits, lies advantageously between 20° and 100° C.

The O-acyl grouping may also be split reductively. Among the applicable processes, the reduction with a complex hydride is especially suitable. The reductive cleavage is carried out in analogy to the procedure described under Method B for reduction of the carboxylic acid amides. It is of advantage to reduce simultaneously the amide and phenol ester grouping.

METHOD H

By ether cleavage of a compound of the formula

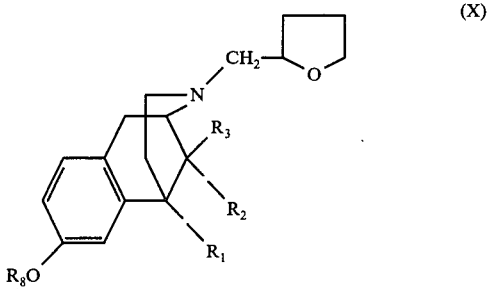

(X)

wherein $R_1$ through $R_3$ have the meanings defined above, and $R_8$ is alkyl or aralkyl, whereby a compound of the formula I wherein $R_4$ is hydrogen is obtained.

The ether cleavage of a compound of the formula X may be effected pursuant to different methods, which vary with the nature of radical $R_8$ and must be chosen in such a way that the tetrahydrofuran ring remains intact. One such suitable method, for example, is the selective cleavage of the phenol ether grouping with caustic soda and caustic potash in a high-boiling-point solvent, such as diethyleneglycol or triethyleneglycol. This reaction is advantageously carried out at temperatures between 150° C and the boiling point of the solvent with an excess of alkali metal hydroxide. Benzyl ethers may also be split by catalytic hydrogenation. Methoxymethyl ethers are very unstable in the presence of acids and can be split even under mild conditions with dilute mineral acids.

METHOD I

By acylation of a compound of the formula I wherein $R_4$ is hydrogen to form a compound of the formula I wherein $R_4$ is acyl.

The acylation may be effected by means of a variety of different methods. Most advantageously, it is effected with a corresponding carboxylic acid chloride or carboxylic acid anhydride in an inert solvent, using the calculated amount or a slight excess of the acylating agent. However, it is also possible to use a greater excess of the acylating agent, which then serves simultaneously as solvent. It is recommended to add to the reaction mixture an acid-binding agent. Pyridine is especially suitable for this purpose; it can be provided in catalytic amounts, in equimolar amounts or in greater excess so as to serve as a solvent. Another base well suited for this purpose is triethylamine. As reaction temperature the range from 20° to 150° C, preferably 50° to 100° C, has proved to be especially suitable.

METHOD K

By alkylating a compound of the formula I wherein $R_4$ is hydrogen to form a compound of the formula I wherein $R_4$ is lower alkyl.

The alkylation may be effected pursuant to a variety of different methods. Preferred alkylating agents and reaction conditions are those which allow for a selective O-alkylation without quaternization of the nitrogen. For this purpose the use of diazoalkanes or phenyl-trialkyl-ammonium-hydroxides as alkylation agents is particularly suitable. With a diazoalkane the alkylation is performed in a suitable inert solvent, such as in diethyl ether or tetrahydrofuran, preferably at room temperature. When using trialkyl-ammonium-hydroxide, the starting compound is heated with the alkylating agent in a suitable inert solvent, preferably in dimethylformamide.

The reaction products of the formula I obtained by the above-described methods A-K are isolated from the reaction mixtures with the aid of conventional procedures. If required, the crude products obtained may be purified by using special processes, such as column-chromatography, before they are crystallized in form of the free bases or suitable acid addition salts.

Depending upon the reaction conditions and reaction partners, the reaction products thus obtained are either sterically uniform compounds or mixtures of racemic or optically active diastereoisomers.

Diastereoisomers may be separated pursuant to known processes, which make use of their differing chemical and physical properties, for example, by fractional crystallization. Racemic compounds may be separated into the corresponding optical antipodes by conventional methods for racemate separation.

Most of the starting compounds needed for methods A-K above are known. Thus, for example, the norbenzomorphans of the formula II are repeatedly described in the literature.

The optically active tetrahydrofurfuryl halides of the formula III may be produced from the known optically active alcohols [F. C. Hartmann and R. Barker, J. Org. Chem. 29, 873–877 (1964)] by halogenation, for instance with phosphorus pentachloride or phosphorus pentabromide (Org. Synth. 23, 88).

| | |
|---|---|
| L-(+)-tetrahydrofurfuryl alcohol: | $[\alpha]_D^{25} = +15.3°$ (c = 5, nitromethane) b.p. 76° Cl 16 mm Hg |
| D-(−)-tetrahydrofurfuryl alcohol: | $[\alpha]_D^{25} = -15.7°$ (c = 5, nitromethane) b.p. 76° C/ 16 mm Hg |
| L-(+)-tetrahydrofurfuryl bromide: | $[\alpha]_D^{25} = -3.8°$ (c = 5, nitromethane) b.p. 67° C/ 16 mm Hg |

By reacting the tetrahydrofurfuryl alcohols with sulfonic acid halides, the corresponding sulfonic acid esters can be prepared.

Carboxylic acid amides of the formula IV are obtained by reacting the nor-compounds of the formula II with tetrahydrofuroyl chlorides. From the corresponding carbonamides of the formula IV the corresponding thiocarbonamides may be produced by reaction with phosphorus pentasulfide.

Compounds of the formula V are obtained by reacting compounds of the formula IV with alkylating agents.

Compounds of the formula VI are produced by reacting nor-compounds of the formula II with β-phenylethyl chloride, naphthylethyl chloride or 1,2-diphenylethyl chloride, and subsequently quaternizing the resulting tertiary amines with compounds of the formula III.

The starting compounds of the formulas VIIa and VIIb are accessible by alkylating piperidines of the formulas

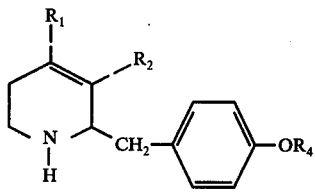 (XI)

or

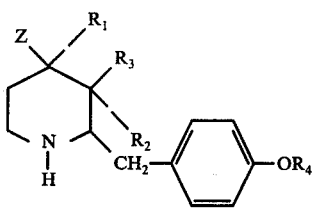 (XII)

wherein $R_1$ through $R_4$ and Z have the meanings previously defined, which are described in the literature, with alkylating agents of the formula III.

The starting compounds of the formula VIII are produced by reacting nor-compounds of the formula II with γ-keto-acid esters of the formula

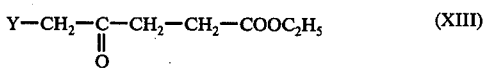 (XIII)

wherein Y has the previously defined meanings, and reducing the intermediate compound of the formula

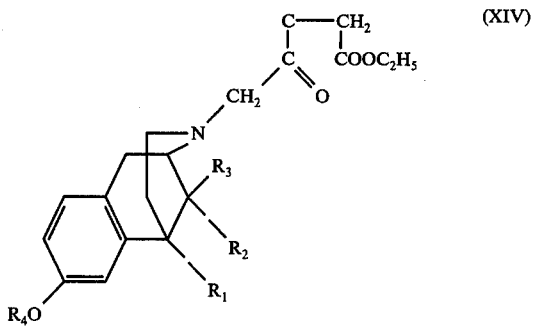 (XIV)

thus obtained with complex hydrides.

The starting compounds of the formulas IX and X are accessible by alkylating corresponding norbenzomorphanes with alkylating agents of the formula III.

The compounds of the formula I are organic bases and therefore form acid addition salts with inorganic or organic acids. Examples of non-toxic, pharmacologically acceptable acid addition salts are those formed with hydrochloric acid, hydrobromic acid, hydro-iodic acid, hydrofluoric acid, sulfuric acid, phosphoric acid, nitric acid, acetic acid, propionic acid, butyric acid, valeric acid, pivalic acid, caproic acid, oxalic acid, malonic acid, succinic acid, maleic acid, fumaric acid, lactic acid, tartaric acid, citric acid, malic acid, benzoic acid, p-amino-benzoic acid, p-hydroxy-benzoic acid, phthalic acid, terephthalic acid, cinnamic acid, salicylic acid, ascorbic acid, 8-chlorotheophylline, methanesulfonic acid, benzenesulfonic acid, ethanephosphoric acid or the like.

The following examples illustrate the present invention and will enable others skilled in the art to understand it more completely. It should be understood, however, that the invention is not limited solely to the particular examples given below. a) Reaction of optically active nor-compounds with optically active tetrahydrofurfuryl compounds.

EXAMPLE 1

(−)-2-(D-Tetrahydrofurfuryl)-[(1R, 5R, 9R)-2'-hydroxy-5,9-dimethyl-6,7-benzomorphan] and its methanesulfonate by method A 2.17 gm (0,01 mol) of (1R, 5R, 9R)-(−)-2'-hydroxy-5,9-dimethyl-6,7-benzomorphan, 1.26 gm of sodium bicarbonate and 1.82 gm (0.011 mol) of D-(−)-tetrahydrofurfuryl bromide were refluxed in a mixture of 15 ml of dimethylformamide and 25 ml of tetrahydrofuran for 75 hours, while stirring. Subsequently, the reaction mixture was evaporated in vacuo, and the residue was shaken with a mixture of 35 ml of chloroform and 35 ml of water. After separation of the chloroform phase in a separating funnel, the aqueous solution was extracted twice with 15 ml of chloroform each. The combined chloroform extracts were washed with 30 ml of water, dried over sodium sulfate and evaporated in vacuo. The crude reaction product thus obtained as the evaporation residue may be crystallized as such or, more preferably, after purification by column-chromatography on aluminum oxide. For column-chromatography the crude product was dissolved in 25 ml of chloroform, and the solution was introduced into a chromatography column charged with 50 gm of aluminum oxide (activity stage III, neutral) in chloroform. The column was eluted with a mixture of 99 parts of volume of chloroform and 1 part of volume of methanol, and the eluate was collected in fractions of 10 to 20 ml. After thin-layer chromatographic examination the fractions containing the pure substance were combined and evaporated in vacuo. The residue was crystallized from a mixture of 10 ml of methanol and 6 ml of water. After standing overnight at 2° C, the crystallizate was collected by suction filtration and washed with a little aqueous methanol. After drying at 80° C, 2.3 gm (76.5% of theory) of the crystalline base, m.p. 197° C, were obtained; its melting point rose to 201° C after recrystallization from aqueous methanol, but did not rise any further after a second recrystallization. The product had a specific rotation of $[\alpha]_D^{25} = -108.5°$ ($c = 1$, methanol).

For conversion into its methanesulfonate, 1.55 gm (0.005 mol) of the crystalline base were dissolved in 8 ml of ethanol by adding 0.47 gm of methanesulfonic acid, and the solution was admixed with absolute ether (40 ml) until turbity just began. After standing for several days in a sealed vessel at 2° C, the salt separated out in the form of coarse crystals. The crystallizate was collected by suction filtration, washed with ethanol/ether (1:1) and then with ether, and dried at 50° C. 1.4 gm (70.5% of theory) of the hygroscopic methanesulfonate were obtained; it had a melting point of 70° C (decomp.) which did not change after recrystallization from ethanol/ether and drying at 50° C in high vacuum.

EXAMPLE 2

Analogous to Example 1, 2.2 gm (72.5% of theory) of (+)-2-(L-tetrahydrofurfuryl)-[(1S,5S,9S)-2'-hydroxy-5,9-dimethyl-6,7-benzomorphan] were obtained, starting from 2.17 gm (0.01 mol) of (1S,5S,9S)-(+)-2'-hydroxy-5,9-dimethyl-6,7-benzomorphan, 1.26 gm of sodium bicarbonate and 1.82 gm (0.011 mol) of L-(+)-tetrahydrofurfuryl bromide, as the first crystallizate from aqueous methanol; the product had a melting point of 199° C, which rose to 200° C after recrystallization from aqueous methanol. The specific rotation of the substance was $[\alpha]_D^{25} = +109.3°$ ($c = 1$, methanol).

EXAMPLE 3

Analogous to Example 1, 2.3 gm (76.5% of theory of (−)-2-(L-tetrahydrofurfuryl)-[(1R,5R,9R)-2'-hydroxy-5,9-dimethyl-6,7-benzomorphan] were obtained, starting from 2.17 gm (0.01 mol) of (1R,5R,9R)-(−)-2'-hydroxy-5,9-dimethyl-6,7-benzomorphan, 1.26 gm of sodium bicarbonate and 1.82 gm (0.011 mol) of L-(+)-tetrahydrofurfuryl bromide, as the first crystallizate from aqueous methanol; the product had a melting point of 133° C, which rose to 137° C after recrystallization from aqueous methanol. The substance had a specific rotation of $[\alpha]_D^{25} = -98.5°$ ($c = 1$, methanol).

EXAMPLE 4

Analogous to Example 1, 2.1 gm (69.5% of theory) of (+)-2-(D-tetrahydrofurfuryl)-[(1S,5S,9S)-2'-hydroxy-5,9-dimethyl-6,7-benzomorphan] were obtained, starting from 2.17 gm (0.01 mol) of (1S,5S,9S)-(+)-2'-hydroxy-5,9-dimethyl-6,7-benzomorphan, 1.26 gm of sodium bicarbonate and 1.82 gm (0.011 mol) of D-(−)-tetrahydrofurfuryl bromide, as the first crystallizate from aqueous methanol; the product had a melting point of 133° C, which rose to 137° C) after recrystallization. The substance had a specific rotation of $[\alpha]_D^{25} = +98.2°$.

b) Reaction of optically active nor-compounds with racemic tetrahydrofurfuryl derivatives.

EXAMPLE 5

(−)-2-(D-tetrahydrofurfuryl-[(1R,5R,9R)-2'-hydroxy-5,9-dimethyl-6,7-benzomorphan] and
(−)-2-(L-tetrahydrofurfuryl)-[(1R,5R,9R)-2'-hydroxy-5,9-dimethyl-6,7-benzomorphan] by method A 21.7 gm (0.1 mol) of (1R,5R,9R)-(−)-2'-hydroxy-5,9-dimethyl-6,7-benzomorphan, 12.6 gm of sodium bicarbonate, 18.2 gm (0.11 mol) of (±)-tetrahydrofurfuryl bromide and 2 gm of potassium iodide were heated at 100° C in 200 ml of dimethylformamide for 18 hours, while vigorously stirring. Subsequently, the reaction solution was cooled and then admixed over a period of 30 minutes with 400 ml of water, while stirring. The crystallizate which precipitated was stirred at room temperature for another 2 hours, and was then collected by suction filtration, washed thoroughly with several portions of water and, after sharp suction-drying, dried at 80° C until weight constance is reached. 21.0 gm of a mixture of the diastereoisomeric compounds named in the heading were obtained. The mother liquor was set aside.

For separation of the diastereoisomers, the crystallizate was recrystallized from 220 ml of methyl ethyl ketone. After cooling overnight at 2° C, the crystals were collected by suction filtration and washed with a little cool methyl ethyl ketone. The mother liquor was set aside, and the crystals were dried at 80° C. 11.7 gm of crystals, m.p. 197° C, were obtained which, after crystallization from a mixture of 270 ml of methanol and 135 ml of water, yielded 10.6 gm of pure (−)-2-(D-tetrahydrofurfuryl)-[(1R,5R,9R)-2'-hydroxy-5,9-dimethyl-6,7-benzomorphan], m.p. 201° C.

The second diastereoisomer was recovered from the dimethylformamide and the methyl ethyl ketone mother liquors. The dimethylformamide mother liquor was evaporated in vacuo, and the residue was crystallized from a mixture of 50 ml of dimethylformamide and 200 ml of water. After standing for 2 days at room temperature, the crystals were collected by suction filtration, washed with water and dried at 80° C, yielding 4.1 gm of the second diastereoisomer in rather pure form.

The methyl ethyl ketone mother liquor was evaporated, and the residue was crystallized from 30 ml of methyl ethyl ketone. After standing overnight at room temperature the mixture was suction-filtered, whereby methyl ethyl ketone mother liquor No. 2 and, after drying at 80° C, 4.4 gm of crystallizate were obtained. The crystallizate was recrystallized from methyl ethyl ketone, whereby methyl ethyl ketone mother liquor No. 3 and 1.4 gm of crystallizate were obtained. The latter consisted of a mixture of the two diastereoisomers in a ratio of about 1:1 and may be subjected again to the above-described separation procedure. Mother liquors No. 2 and No. 3 were combined and evaporated in vacuo. The evaporation residue consisted, like the second crystallizate (4.1 gm) isolated from the dimethylformamide mother liquor, of the second diastereoisomer. They were combined and crystallized from a mixture of toluene and gasoline (b.p. range 60°–80° C) in a volumetric ratio of 70:30. After standing overnight at room temperature, the crystals were collected by suction filtration and washed with gasoline. After drying at 80° C, 6.5 gm of (−)-2-(L-tetrahydrofurfuryl)-[(1R,5R,9R)-2'-hydroxy-5,9-dimethyl-6,7-benzomorphan], m.p. 137° C, were obtained. Upon crystallization of the evaporation residue of the mother liquor from 50 ml of toluene/gasoline, another 2.7 gm of the same substance with the same melting point were obtained. The total yield of the second diastereoisomer was thus 9.2 gm.

EXAMPLE 6

Analogous to Example 1, (−)-2-tetrahydrofurfuryl-2'-hydroxy-5,9,9-trimethyl-6,7-benzomorphan methanesulfonate was obtained, starting from 1.16 gm (0.005 mol) of (±)-2'-hydroxy-5,9,9-trimethyl-6,7-benzomorphan and 0.91 gm of D-(−)-tetrahydrofurfuryl bromide; it had a melting point of 182° C, which did not change after recrystallization from ethanol/ether. It was one of the two optically active diastereoisomers. The other one was isolated from the mother liquor.

c) Reaction of racemic nor-compounds with racemic tetrahydrofurfuryl derivatives.

EXAMPLE 7

(±)-2-Tetrahydrofurfuryl-2'-hydroxy-5,9α-dimethyl-6,7-benzomorphan (racemic diastereoisomers I and II) by method A 21.7 gm (0.1 mol) of (±)-2'-hydroxy-5,9α-dimethyl-6,7-benzomorphan, 13.7 gm of sodium bicarbonate, 19.9 gm (0.12 mol) of (±)-tetrahydrofurfuryl bromide and 2 gm of potassium iodide were heated in 200 ml of dimethylformamide at 100° C for 18 hours, while vigorously stirring. Subsequently, the reaction solution was cooled, admixed with 400 ml of water over a period of 2 hours, suction-filtered and the filter cake was washed with water several times. After sharp suction filtration and drying at 80° C, 25.4 gm of a crystallizate were obtained, which consisted of the two racemic diastereoisomers I and II. The mother liquor was discarded.

The racemic diastereoisomers I and II were separated in the form of their hydrochlorides as follows: The mixture of diastereoisomers was dissolved in 100 ml of ethanol by addition of 7.3 ml of concentrated hydrochloric acid. Crystallization started immediately. After standing overnight, the crystals were collected by suction filtration, washed with ethanol/ether 1:1 and then with ether, and dried first in the air and then at 80° C. 13.5 gm of the not yet completely pure hydrochloride of diastereoisomer I and mother liquor No. 1 were obtained. Recrystallization of the hydrochloride from 350 ml of ethanol yielded 8.1 gm of pure substance, m.p. 294° C, and mother liquor No. 2. Evaporation of mother liquor No. 2 to 100 ml yielded 2.6 gm of a crystallizate with a m.p. of 287°–288° C and mother liquor No. 3. The latter was evaporated in vacuo together with mother liquor No. 1, and the residue was crystallized from 50 ml of ethanol, whereby 1.5 gm of a substance with a m.p. of 287°–288° C and mother liquor No. 4 were obtained. The crystallizates having a melting point of 287°–288° C were combined (4.1 gm) and recrystallized from 40 ml of ethanol, whereby another 2.9 gm of the pure hydrochloride of diastereoisomer I, m.p. 294° C, and mother liquor No. 5 were obtained. Thus, the total yield of pure hydrochloride, m.p. 294° C, amounted to 11.0 gm.

The diastereoisomer II was isolated from mother liquors Nos. 3, 4 and 5 as follows: The combined mother liquors were evaporated in vacuo, and the residue was extracted with a mixture of 75 ml of chloroform, 75 ml of water and 10 ml of concentrated ammonia. After separation of the chloroform phase in a separator funnel, the aqueous phase was extracted once more with 25 ml of chloroform. The combined chloroform extracts were washed with water, dried with sodium sulfate and evaporated in vacuo. The residue consisted of the crude free base of the second diastereoisomer. It was crystallized from 100 ml of a mixture of toluene and gasoline (b.p. range 60°–80° C) in a volumetric ratio of 70:30. After standing overnight at room temperature, the crystals were collected by suction filtration, washed with a little cold toluene/gasoline, then with only gasoline, and dried at 80° C. 10.6 gm of the pure diastereoisomer II, m.p. 166° C, were obtained. The evaporated filtrate yielded as a residue 3.5 gm of a mixture of the two diastereoisomers, which may again be subjected to the above-described separation procedure. Thus, a total of 11.0 gm of (±)-2-tetrahydrofurfuryl-2'-hydroxy-5,9α-dimethyl-5,7-benzomorphan hydrochloride (diastereoisomer I) and 10.6 gm of (±)-2-tetrahydrofurfuryl-2'-hydroxy-5,9α-dimethyl-6,7-benzomorphan (diastereoisomer II) were obtained.

Upon splitting of the racemates into their optical antipodes, diastereoisomer I yielded the compounds described in Examples 1 and 2, the diastereoisomer II yielded the compounds described in Examples 3 and 4.

EXAMPLE 8

(+)-2-Tetrahydrofurfuryl-2'-hydroxy-5,9α-dimethyl-6,7-benzomorphan (racemic diastereoisomer I) by method A 2.18 gm (0.01 mol) of 2'-hydroxy-5,9α-dimethyl-6,7-benzomorphan, 1.26 gm of sodium bicarbonate and 2.82 gm (0.011 mol) of tetrahydrofurfuryl p-toluenesulfonate were refluxed in a mixture of 20 ml of dimethylformamide and 25 ml of tetrahydrofuran for 6 hours, while stirring. Then the reaction mixture was filtered while still warm, and the filtrate was evaporated in vacuo at about 50° C to remove the tetrahydrofuran. After addition of 40 ml of water, the mixture of diastereoisomers described in Example 7 crystallized out, which was separated in the manner described there, yielding 1.0 gm of the hydrochloride of diastereoisomer I, m.p. 294° C. For conversion into the free base, the hydrochloride was dissolved in 10 ml of water, and the solution was made alkaline by dropwise addition of 1 N ammonia, while stirring, whereby the free base precipitated out. After standing overnight at room temperature, the precipitate was collected by vacuum filtration, washed with water and, after sharp suction filtration recrystallized from a mixture of 20 ml of methanol and 7 ml of water, yielding 0.75 gm of the desired compound having a melting point of 175°–176° C, which remained unchanged after recrystallization from aqueous methanol.

EXAMPLE 9

Analogous to Example 1, (±)-2-tetrahydrofurfuryl-2'-hydroxy-5,9,9-trimethyl-6,7-benzomorphan methanesulfonate (racemic diastereoisomer I) was obtained, starting from 1.16 gm (0.005 mol) of (±)-2'-hydroxy-5,9,9-trimethyl-6,7-benzomorphan and 0.91 gm (0.0055 mol) of (±)-tetrahydrofurfuryl bromide, the product had a m.p. of 207°–210° C which rose to 210° C after recrystallization from ethanol/ether. It was one of the two racemic diastereoisomers; the other one was isolated from the mother liquors.

EXAMPLE 10

(±)-2-Tetrahydrofurfuryl-2'-hydroxy-5-methyl-9α-ethyl-6,7-benzomorphan by method A 2.31 gm (0.01 mol) of (±)-2'-hydroxy-5-methyl-9α-ethyl-6,7-benzomorphan, 1.3 gm of sodium bicarbonate, 1.97 gm (0.012 mol) of (±)-tetrahydrofurfuryl bromide and 0.2 gm of sodium iodide were refluxed in a mixture of 15 ml of dimethylformamide and 25 ml of tetrahydrofuran for 60 hours, while stirring. The reaction product was isolated as indicated in Example 1, purified by chromatography on 75 gm of aluminum oxide, and crystallized from aqueous methanol. Yield: 1.2 gm. After recrystallization from 20 ml of methanol and 5 ml of water, the melting point of 171° C did not change. The crystallized substance thus obtained was one of the two racemic diastereoisomers formed by the reaction. The other one was isolated from the mother liquors.

EXAMPLE 11

(±)-2-Tetrahydrofurfuryl-2'-hydroxy-5-ethyl-9α-methyl-6,7-benzomorphan by method A Starting from 2.31 gm (0.01 mol) of (±)-2'-hydroxy-5-ethyl-9α-methyl-6,7-benzomorphan and 1.97 gm (0.012 mol) of (±)-tetrahydrofurfuryl bromide, and using a procedure analogous to that of Example 10, yielded 1.3 gm of the compound named in the heading which had a melting point of 170° C; it did not change after recrystallization from 30 ml of methanol and 10 ml of water. The crystallized substance thus obtained was one of the two racemic stereoisomers formed by the reaction. The other one was isolated from the mother liquors.

EXAMPLE 12

(±)-2-Tetrahydrofurfuryl-2'-hydroxy-5,9α-diethyl-6,7-benzomorphan hydrochloride by method A Starting from 2.45 gm (0.01 mol) of (±)-2'-hydroxy-5,9α-diethyl-6,7-benzomorphan and 1.97 gm (0.012 mol) of (±)-tetrahydrofurfuryl bromide, a reaction product was obtained which was purified by chromatography on aluminum oxide in analogy to Example 10. The free base thus obtained was dissolved in 10 ml of absolute ethanol and, after acidification with 2 N ethanolic hydrochloric acid, the solution was admixed with absolute ether until it became turbid. The hydrochloride crystallized out, which was collected by suction filtration after standing overnight, washed first with ethanol/ether (1:1) and then with only ether, and dried at 80° C. 1.0 gm of the compound named in the heading was obtained; it had a melting point of 239° C, which did not change after recrystallization from ethanol/ether. The substance thus obtained was the hydrochloride of one of the racemic diastereoisomers formed by the reaction. The other one was isolated from the mother liquor.

EXAMPLE 13

Analogous to Example 1, 2.1 gm of (±)-2-tetrahydrofurfuryl-2'-hydroxy-5-methyl-6,7-benzomorphan methanesulfonate were obtained, starting from 2.03 gm (0.01 mol) of (±)-2'-hydroxy-5-methyl-6,7-benzomorphan and 1.97 gm (0.012 mol) of (±)-tetrahydrofurfuryl bromide; the product had a melting point of 171°–172° C, which did not change after recrystallization from a mixture of 5 ml of ethanol and diethyl ether. The substance thus obtained was one of the two racemic diastereoisomers formed by the reaction. The other one was isolated from the mother liquor.

EXAMPLE 14

Analogous to Example 10, 2.0 gm of (±)-2-tetrahydrofurfuryl-2'-hydroxy-5-ethyl-6,7-benzomorphan were obtained, starting from 2.17 gm (0.01 mol) of (±)-2'-hydroxy-5-ethyl-6,7-benzomorphan and 1.97 gm (0.012 mol) of (±)-tetrahydrofurfuryl bromide; the product had a melting point of 150°–151° C, which did not change after recrystallization from a mixture of 40 ml of acetone and 30 ml of water. The substance thus obtained was one of the two racemic diastereoisomers formed by the reaction. The other one was isolated from the mother liquor.

EXAMPLE 15

Analogous to Example 10, 2.1 gm of (±)-2-tetrahydrofurfuryl-2'-hydroxy-5-n-propyl-6,7-benzomorphan were obtained, starting from 2.31 gm (0.01 mol) of (±)-2'-hydroxy-5-n-propyl-6,7-benzomorphan and 1.97 gm (0.012 mol) of (±)-tetrahydrofurfuryl bromide; the product had a melting point of 152° C, which did not change after recrystallization from a mixture of 30 ml of methanol and 40 ml of water. The substance thus obtained was one of the two racemic diastereoisomers formed by the reaction. The other one was isolated from the mother liquor.

EXAMPLE 16

(±)-2-Tetrahydrofurfuryl-2'-hydroxy-5,9α-dimethyl-6,7-benzomorphan (racemic diastereoisomers I and II) by method B 21.7 gm (0.1 mol) of (±)-2'-hydroxy-5,9α-dimethyl-6,7-benzomorphan were dissolved in 400 ml of methanol while heating the same, and the solution was admixed at room temperature, while vigorously stirring, with a solution of 25 gm of potassium carbonate in 40 ml of water. A fine crystalline mixture consisting of some of the base and the carbonate precipitated out. While the vigorous stirring was continued, 22.2 gm (0.165 mol) of tetrahydrofuran-2-carboxylic acid chloride were added dropwise to the suspension over a period of 30 minutes, and the mixture was stirred for another hour. Then it was evaporated in vacuo, and the residue was extracted with a mixture of 150 ml of chloroform and 100 ml of water. The aqueous phase was separated from the chloroform layer in a separating funnel and was again extracted with 50 ml of chloroform. The combined chloroform extracts were washed first with 100 ml of 1 N HCl and then with 100 ml of water, dried with sodium sulfate, and evaporated in vacuo after addition of 50 ml of toluene. The residue consisted of 2-(tetrahydro-2-furoyl)-2'-hydroxy-5,9α-dimethyl-6,7-benzomorphan, which was used as such for the following reduction:

The evaporation residue was dissolved in 250 ml of absolute tetrahydrofuran, and the solution was added dropwise over a period of 20 minutes to a suspension of 12 gm of lithium aluminum hydride in 150 ml of ice-cold absolute tetrahydrofuran, while stirring. Subsequently, the ice bath was removed, stirring was continued for 1 hour at room temperature, and then it was refluxed for 2 hours. Thereafter, the mixture was cooled and, while stirring and cooling on ice, it was admixed dropwise with 50 ml of water. Then, 1200 ml of an aqueous saturated diammoniumtartrate solution were added, the mixture was shaken in a separating funnel and, after settling, the (upper) tetrahydrofuran phase was separated from the heavier aqueous layer. The tetrahydrofuran solution was evaporated in vacuo, and the aqueous solution was extracted with 100 ml of chloroform. The chloroform extract was used to dissolve the evaporation residue of the tetrahydrofuran solution, and the resulting solution was washed with water, dried with sodium sulfate and evaporated in vacuo. The residue was the crude diastereoisomer mixture, which was separated with the aid of 8 ml of concentrated hydrochloric acid and 100 ml of ethanol via the hydrochlorides, as described in Example 6. The separation yielded 11.3 gm of the pure hydrochloride of diastereoisomer I, m.p. 294° C, and 9.3 gm of the diastereoisomer II (free base) having a melting point of 166° C.

EXAMPLE 17

(−)-2-(D-Tetrahydrofurfuryl)-[(1R,5R,9R)-2′-hydroxy-5,9-dimethyl-6,7-benzomorphan] and (−)-2-(L-tetrahydrofurfuryl-[(1R,5R,9R)-2′-hydroxy-5,9-dimethyl-6,7-benzomorphan] by method B A suspension of 8.7 gm (0.04 mol) of (1R,5R,9R)-(−)-2′-hydroxy-5,9-dimethyl-6,7-benzomorphan in a mixture of 87 ml of absolute methylenechloride and 16 ml of triethylamine was admixed dropwise, while stirring, over a period of 15 minutes at room temperature in a vessel equipped with an upright reflux-cooler with a solution of 11.9 gm (0.88 mol) of tetrahydrofuran-2-carboxylic acid chloride in 40 ml of absolute methylene chloride. Then, the reaction mixture was refluxed for 2 hours. Afterwards, it was cooled, washed twice with 30 ml of water each, dried with sodium sulfate and evaporated in vacuo. The residue consisted of crude 2-(tetrahydro-2-furoyl)-2′-(tetrahydro-2-furoyloxy)-5,9-dimethyl-6,7-benzomorphan, which was used as such for the following reduction:

Analogous to Example 16, the evaporation residue was reduced with 5.0 gm of lithiumaluminum hydride, and the reduction product was isolated from the tetrahydrofuran phase and the chloroform extract of the diammoniumtartrate solution, as described there. It consisted of a mixture of the crude compounds named in the heading, which were separated from each other analogous to Example 5, yielding 4.8 gm of pure (−)-2-(D-tetrahydrofurfuryl)-[(1R,5R,9R)-2′-hydroxy-5,9-dimethyl-6,7-benzomorphan] having a m.p. of 201° C, and 3.4 gm of pure (−)-2-(L-tetrahydrofurfuryl)-[(1R,5R,9R)-2′-hydroxy-5,9-dimethyl-6,7-benzomorphan] having a m.p. of 137° C.

EXAMPLE 18

(−)-2-(D-Tetrahydrofurfuryl)-[(1R,5R,9R)-2′-hydroxy-5,9-dimethyl-6,7-benzomorphan] and (−)-2-(L-tetrahydrofurfuryl-[(1R,5R,9R)-2′-hydroxy-5,9-dimethyl-6,7-benzomorphan] by method B Analogous to Example 16, 4.34 gm (0.02 mol) of (1R,5R,9R)-(−)-2′-hydroxy-5,9-dimethyl-6,7-benzomorphan were converted into the corresponding 2-(tetrahydro-2-furoyl) derivative. 8.3 gm of crude product were obtained as the evaporation residue, which was thionated as follows to form the corresponding 2-(tetrahydro-2-thiofuroyl) derivative:

The residue was dissolved in 100 ml of absolute pyridine, and the solution was refluxed with 2.6 gm of phosphorus pentasulfide for 3 hours. Subsequently, the reaction solution was evaporated in vacuo, and the residue was shaken with a mixture of 100 ml of methylene chloride and 100 ml of water. After isolation in a separating funnel, the aqueous phase was extracted once more with 50 ml of methylene chloride. The combined methylene chloride extracts were washed, in the presence of ice, first once with 30 ml of 2 N HCl and then three times with 30 ml of water each, dried with sodium sulfate and evaporated in vacuo. The residue consisted of the crude 2-(tetrahydro-2-thiofuroyl) derivative (5.2 gm).

Analogous to Example 16, the evaporation residue of the methylene chloride extracts was reduced with 1.5 gm of lithium aluminum hydride. The reduction product was purified by column-chromatography on aluminum oxide, as described in Example 1, yielding a mixture of the two pure compounds named in the heading. Separation was effected as described in Example 5, yielding 0.6 gm of (−)-2-(D-tetrahydrofurfuryl) and 0.5 gm of (−)-2-(L-tetrahydrofurfuryl-[(1R,5R,9R)-2′-hydroxy-5,9-dimethyl-6,7-benzomorphan] having melting points of 201° and 137° C, respectively.

EXAMPLE 19

(−)-2-(D-Tetrahydrofurfuryl)-[(1R,5R,9R)-2′-hydroxy-5,9-dimethyl-6,7-benzomorphan] and (−)-2-(L-tetrahydrofurfuryl-[(1R,5R,9R)-2′-hydroxy-5,9-dimethyl-6,7-benzomorphan] by method C 4.34 gm (0.02 mol) of (1R,5R,9R)-(−)-2′-hydroxy-5,9-dimethyl-6,7-benzomorphan were converted into the corresponding 2-(tetrahydro-2-thiofuroyl) derivative analogous to Example 18. The product was refluxed under exclusion of moisture in 120 ml of absolute acetone with 6.3 gm of methyliodide for 2 hours. The reaction product was precipitated with 600 ml of absolute ether, and the supernatant solution was decanted after settling. In this manner the methoiodide of the 2-(tetrahydro-2-thiofuroyl) compound was obtained, which was reduced with sodium borohydride as follows:

40 ml of absolute ethanol were added to the precipitate and then, while stirring, 2.3 gm of finely pulverized sodium borohydride were added in 5 portions over a period of 5 minutes. The temperature rose from 23°–53° C within the first 15 minutes. After a total reaction time of 1 hour, the reaction mixture was cooled and then admixed dropwise with 100 ml of 2 N HCl, and subsequently refluxed for 30 minutes. Afterwards, the reaction solution was cooled, made alkaline with concentrated ammonia, and extracted with 100 ml of chloroform. After isolation in a separating funnel, the aqueous phase was once more extracted with 50 ml of chloroform, and the combined chloroform extracts were washed twice with water, dried with sodium sulfate and evaporated in vacuo. As described in Example 1, the residue was purified by column-chromatography on aluminum oxide, whereby a mixture of the two pure compounds named in the heading was obtained. Upon separation in analogy to Example 5, 0.4 gm of (−)-(D-tetrahydrofurfuryl)- and 0.25 gm of (−)-(L-tetrahydrofurfuryl)-[(1R,5R,9R)-2′-hydroxy-5,9-dimethyl-6,7-benzomorphan] having melting points of 201° and 137° C, respectively, were obtained.

EXAMPLE 20

(±)-2-Tetrahydrofurfuryl-2′-hydroxy-5,9α-dimethyl-6,7-benzomorphan (racemic diastereoisomers I and II) by method E (a) 1-Tetrahydrofurfuryl-2-(p-methoxybenzyl)-3,4-dimethyl-4-hydroxy-piperidine (mixture of isomers)

24.9 gm (0.1 mol) of 2-(p-methoxybenzyl)-3,4-dimethyl-4-hydroxy-piperidine were stirred in 200 ml of dimethylformamide in the presence of 12.6 gm of sodium bicarbonate for 24 hours at 100° C with 19.7 gm (0.12 mol) of tetrahydrofurfuryl bromide. Subsequently, the reaction mixture was evaporated in vacuo, and the residue shaken with a mixture of 150 ml of chloroform and 100 ml of water. After isolation in a separating funnel, the aqueous phase was extracted once more with 50 ml of chloroform. The combined chloroform extracts were washed with water, dried with sodium sulfate and evaporated in vacuo. In analogy to the procedure described in Example 1, the residue was purified by column-chromatography on aluminum oxide (700 gm, activity stage III, neutral), using chloroform as the flow agent.

After evaporation of the combined eluates comprising the pure product, a residue of 16 gm was obtained, which was further reacted as such in the following step.

(b) Cyclization of the benzomorphan ring 16.0 gm of 1-tetrahydrofurfuryl-2-(p-methoxybenzyl)-3,4-dimethyl-4-hydroxy-piperidine (evaporation residue from the preceding step) were stirred with 80 gm of crystallized phosphoric acid in a nitrogen atmosphere at 130° C for 26 hours. Then, the reaction mixture was diluted with 85 ml of water and refluxed for 5 hours. After cooling, it was admixed with 150 ml of benzene, 150 ml of n-butanol and 165 ml of concentrated ammonia, and the mixture was thoroughly shaken. The organic phase was isolated in a separating funnel, and the aqueous phase was extracted twice with benzene/n-butanol. The combined organic phases were washed with water three times, dried with sodium sulfate and evaporated in vacuo. The residue (10 gm) was dissolved in 50 ml of chloroform, and the solution was charged into a chromatography column, containing 200 gm of aluminum oxide (activity stage III, neutral) and was further processed as described in Example 1. The fractions containing the pure substance, as determined by thin-layer chromatography, were combined and evaporated in vacuo, leaving 4.0 gm of a residue which consisted of a mixture of the two stereoisomers I and II. The mixture was separated into its pure components in analogy to Example 5, yielding 1.9 gm of the stereoisomer I as its hydrochloride having a melting point of 294° C, and 1.3 gm of the stereoisomer II as its free base having a melting point of 166° C.

EXAMPLE 21

(+)-2-(Tetrahydrofurfuryl-2'-hydroxy-5,9α-dimethyl-6,7-benzomorphan (racemic diastereoisomers I and II) by method F (a) (+)-2-(2-Oxo-4-ethoxycarbonyl-butyl)-2'-hydroxy-5,9α-dimethyl-6,7-benzomorphan hydrochloride 10.85 gm (0.05 mol) of (+)-2'-hydroxy-5,9α-dimethyl-6,7-benzomorphan, 4.6 gm of sodium bicarbonate and 12.3 gm (0.055 mol) of ethyl 5-bromo-levulinate were refluxed in a mixture of 50 ml of dimethylformamide and 125 ml of tetrahydrofuran, for 2 hours, while stirring. Subsequently, the reaction solution was evaporated in vacuo, and the residue was extracted with a mixture of 250 ml of chloroform and 100 ml of water. The aqueous phase was isolated in a separating funnel and extracted once more with chloroform (50 ml), and the combined chloroform extracts were washed with water, dried with sodium sulfate and evaporated in vacuo. The residue was dissolved in a mixture of 75 ml of ethanol and 25 ml of 2 N ethanolic HCl, and the solution was admixed with absolute ether until turbidity began. After standing overnight, the crystalline substance which had separated out was suction-filtered off at 2° C and washed with ethanol/ether (1:1) and then with only ether. Afterwards, the crystallizate was dried first in the air and then at 80° C, yielding 18.2 gm (92% of theory) of the compound named in the heading, which had a melting point of 212°–215° C. A sample, recrystallized from ethanol/ether, melted at 214°–216° C. The melting point did not change after another recrystallization.

(b) (±)-2-(2,5-dihydroxy-n-pentyl)-2'-hydroxy-5,9α-dimethyl-6,7-benzomorphan (mixture of stereoisomers)

19.8 gm (0.05 mol) of (±)-2-(2-oxo-4-ethoxycarbonylbutyl)-2'-hydroxy-5,9α-dimethyl-6,7-benzomorphan hydrochloride were converted into the free base by shaking with a mixture of 100 ml of chloroform, 100 ml of water and 7 ml of concentrated ammonia; the base dissolved in the chloroform phase. After separation of the chloroform phase, the aqueous phase was extracted once more with 25 ml of chloroform, and the chloroform extracts were combined, washed with water, dried over sodium sulfate and evaporated in vacuo. The residue was reduced with lithium aluminum hydride. For this purpose a solution of the evaporation residue in 100 ml of absolute tetrahydrofuran was added dropwise, while stirring and cooling on ice, over a period of an hour to a suspension of 2.9 gm of lithium aluminum hydride in 250 ml of absolute tetrahydrofuran. Stirring was then continued for another hour at room temperature, and the mixture was then refluxed for 3 hours. Subsequently, it was allowed to cool and, while stirring and cooling on ice, it was admixed dropwise with 10 ml of water and then with 290 ml of an aqueous saturated diammoniumtartrate solution. After shaking it well, the two-phase mixture was separated in a separating funnel. The (upper) tetrahydrofuran phase was evaporated in vacuo, and the aqueous phase was extracted twice with 100 ml of chloroform each. The combined chloroform extracts were used to take up the evaporation residue of the tetrahydrofuran phase, and the resulting solution was washed twice with water, dried with sodium sulfate and evaporated in vacuo. The residue (17.5 gm) was purified by column-chromatography, using 350 gm of aluminum oxide (activity stage III, neutral), in analogy to the procedure described in Example 1. First, the column was eluted with chloroform, then with a mixture of chloroform and methanol in a volumetric ratio of 99:1, the eluates being collected in fractions of 25 ml each. After thin-layer chromatographic determination, the fractions containing the pure desired product were combined and evaporated in vacuo, leaving as a residue the main product of the reduction consisting of a mixture of stereoisomers (17.5 gm).

(c) (±)-2-Tetrahydrofurfuryl-2'-hydroxy-5,9α-dimethyl-6,7-benzomorphan (racemic diastereoisomers I and II The evaporation residue of the preceding step (17.5 gm) was refluxed with 17.5 gm of p-toluenesulfonic acid in 800 ml of xylene for 45 minutes in a vessel equipped with a water trap. Subsequently, the reaction solution was evaporated in vacuo, and the residue was extracted with a mixture of 100 ml of chloroform, 50 ml of water and 10 ml of concentrated ammonia. After isolation in a separating funnel, the aqueous phase was extracted once more with 25 ml of chloroform. The combined chloroform extracts were washed twice with 30 ml of water each, dried with sodium sulfate and evaporated in vacuo. The evaporation residue was purified by column-chromatography on 500 gm of aluminum oxide (activity stage III, neutral), using the method described in Example 1. The column was eluted with chloroform/methanol, first in a volumetric ratio of 99:1 for separation of the faster flowing impurities, and then in a volumetric ratio of 95:5. The fractions comprising the pure reaction products were combined and evaporated in vacuo, leaving 12 gm of a residue which contained some residual solvents. The residue was subjected to the procedure for separation of the two diastereoisomers described in Example 7, which yielded the hydrochloride of diastereoisomer I (2.4 gm) and the free base of diastereoisomer II (2.2 gm). After recrystallization, their melting points of 284° C and 161° C, respectively, rose to 294° C and 166° C, respectively.

EXAMPLE 22

(±)-2-Tetrahydrofurfuryl-2'-hydroxy-5,9α-dimethyl-6,7-benzomorphan (racemic diastereoisomers I and II) by method C (a) (±)-2-Tetrahydrofurfuryl-2'-hydroxy-5,9α-dimethyl-6,7-benzomorphan (mixture of diastereoisomers)

Analogous to Example 8, 3.21 gm (0.01 mol) of 2'-benzoyloxy-5,9α-dimethyl-6,7-benzomorphan are alkylated in the presence of 0.95 gm of sodium bicarbonate in dimethylformamide/tetrahydrofuran with 2.82 gm of tetrahydrofurfuryl p-toluenesulfonate. Subsequently, the reaction solution was evaporated in vacuo, and the residue extracted with a mixture of 50 ml of chloroform and 50 ml of water. After isolation in a separating funnel, the aqueous phase was extracted once with 25 ml of chloroform. The combined chloroform extracts were washed with water, dried with sodium sulfate and evaporated in vacuo, leaving as a residue a mixture of the two racemic, diastereoisomeric (±)-2-tetrahydrofurfuryl-2'-benzoyloxy -5,9α-dimethyl-6,7-benzomorphans.

(b) (±)-2-Tetrahydrofurfuryl-2'-hydroxy-5,9α-dimethyl-6,7-benzomorphan (racemic diastereoisomers I and II)

The evaporation residue of the preceding synthesis step was dissolved in 75 ml of methanol, and the solution was refluxed for 15 minutes after addition of 20 ml of 2 N NaOH. Then, it was acidified with 25 ml of 2 N HCl and evaporated in vacuo. The residue was extracted with a mixture of 50 ml of chloroform, 50 ml of water and 2 ml of concentrated ammonia. After isolation in a separating funnel, the aqueous phase was extracted once more with 25 ml of chloroform. The combined chloroform extracts were washed with water, dried with sodium sulfate and evaporated in vacuo. The residue consisted of the two racemic diastereoisomers I and II, which were separated by crystallization of their hydrochlorides, analogous to Example 7. Thus, the hydrochloride of diastereoisomer I having a melting point of 294° C, was obtained with a yield of 0.7 gm, and the diastereoisomer II having a melting point of 166° C was obtained with a yield of 0.4 gm.

EXAMPLE 23

(±)-2-Tetrahydrofurfuryl-2'-hydroxy-5,9α-dimethyl-6,7-benzomorphan (racemic diastereoisomer I) by method H 2.0 gm (0.0062 mol) of (±)-tetrahydrofurfuryl-2'-methoxy-5,9α-dimethyl-6,7-benzomorphan (O-methyl derivative of the compound named in the heading) were heated at 210° C with 2 gm of finely pulverized potassium hydroxide in 20 ml of diethyleneglycol for 4 hours. After cooling, the reaction mixture was diluted with 100 ml of water, acidified with concentrated hydrochloric acid, made alkaline with concentrated ammonia, and extracted with 50 ml of chloroform. The aqueous phase was isolated in a separating funnel, and extracted twice with 25 ml of chloroform each. The three chloroform extracts were combined, washed with water, dried with sodium sulfate and evaporated in vacuo. The residue, after crystallization from aqueous methanol, yielded 1.7 gm (89% of theory) of the compound named in the heading having a m.p. of 173°-175° C, which rose to 176° C after recrystallization from aqueous methanol.

EXAMPLE 24

(−)-2-(D-Tetrahydrofurfuryl)-[(1R,5R,9R)-2'-acetoxy-5,9-dimethyl-6,7-benzomorphan] by method I 3.0 gm (0.01 mol) of (−)-2-(D-tetrahydrofurfuryl)-[(1R,5R,9R)-2'-hydroxy-5,9-dimethyl-6,7-benzomorphan] were heated on a boiling water bath with 25 ml of acetic acid anhydride for 30 minutes. Subsequently, the reaction solution was evaporated in vacuo, and the residue was stirred for several minutes with a mixture of 100 gm of ice and 100 ml of water. After addition of 100 ml of ether, the mixture was made just alkaline with 2 N ammonia, while stirring was continued. The ether phase was separated, and the aqueous phase was once more extracted with 50 ml of ether. The combined ethereal extracts were washed with water, dried thoroughly with sodium sulfate and evaporated in vacuo, leaving the compound named in the heading in the form of a yellowish syrup. The product was thin-layer chromatographically pure and an $R_f$-value of 0.5, compared to the $R_f$-value of 0.25 of the starting compound (silicagel; chloroform/methanol/concentrated ammonia = 90:10:0.5).

EXAMPLE 25

(±)-2-Tetrahydrofurfuryl-2'-methoxy-5,9α-dimethyl-6,7-benzomorphan (O-methyl derivative of the diastereoisomer I from Example 7) by method K 3.37 gm (0.01 mol) of (±)-2-tetrahydrofurfuryl-2'-hydroxy-5,9-dimethyl-6,7-benzomorphan hydrochloride (diastereoisomer I from Example 7) and 1.9 gm (0.011 mol) of phenyltrimethyl-ammonium chloride were dissolved together in 100 ml of methanol, and the solution was admixed, while stirring, with 1.08 gm (0.02 mol) of sodium methylate. Sodium chloride precipitated out, which was separated by suction filtration after 2 hours' stirring. The filtrate was evaporated, the residue was dissolved in dimethylformamide, and the solution was evaporated again. Then, fresh dimethylformamide (30 ml) was added, and the reaction mixture was refluxed for 2 hours. After cooling, it was evaporated, and the residue was shaken in a separating funnel with a mixture of 50 ml of 2 N NaOH and 50 ml of chloroform. After separation of the phases, the aqueous phase was extracted twice with 50 ml of chloroform each. The combined chloroform phases were washed with water, dried with sodium sulfate and evaporated in vacuo. The residue was purified by chromatography on 200 gm of silicagel, using as the flow agent chloroform/methanol/concentrated ammonia in a volumetric ratio of 90:10:0.5. For this purpose, the evaporation residue was dissolved in 20 ml of the flow agent, and the solution was chromatographed on a silicagel column which had been prepared using the above-mentioned flow agent. The column was eluted, and the eluate was collected in fractions of 25 ml. After examination by thinlayer chromatogram, the fractions containing the pure product were combined and evaporated in vacuo. The residue was dissolved in a little ethanol, and the solution was acidified with ethanol hydrochloric acid and admixed with ether until turbidity began. The hydrochloride crystallized out, and was collected by suction filtration after standing overnight at 2° C, washed first with ethanol/ether (1:1) and then with ether, and dried at 80° C. 1.5 gm of the compound named in the heading, having a melting point of 207°-208° C which did not change after recrystallization from ethanol/ether, were obtained.

The compounds of the present invention, that is, those embraced by formula I above and their non-toxic, pharmacologically acceptable acid addition salts, have useful pharmacodynamic properties. More particularly, the compounds of this invention exhibit strong analgesic activities in warm-blooded animals, such as mice. In various pharmacological tests on mice, such as the Haffner test, the hot-plate test and the writhing test, the analgesic activity of the compounds of the present invention was found to be ten to thirty times greater than that of morphine. However, they differ from morphine by the absence of the typical morphine side-effects in mice, such as Straub's tail, running in circles and the like, which, according to current literature teachings, is strongly indicative of the absence of addictive properties [see, for example, I. Schemano et al, *A Rapid Screening Test for Potential Addiction Liability of New Analgesic Agents*, Toxicol. Appl. Pharmacol. 6, 334–339 (1964)]. In addition, the compounds of this invention exhibit a significantly greater therapeutic ratio than morphine and produce no morphine-like effects in morphine-addicted rats.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from about 0.0083 to 1.67 mgm/kg body weight, preferably 0.016 to 0.33 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 26

Tablets

The tablet composition is compounded from the following ingredients:

| | |
|---|---|
| (−)-2-(D-Tetrahydrofurfuryl)-[(1R,5R,9R) -2'-hydroxy-5,9-dimethyl-6,7-benzomorphan]methanesulfonate | 20.0 parts |
| Lactose | 120.0 parts |
| Corn starch | 50.0 parts |
| Colloidal silicic acid | 2.0 parts |
| Soluble starch | 5.0 parts |
| Magnesium stearate | 3.0 parts |
| Total | 200.0 parts |

Preparation:

The benzomorphan compound is intimately admixed with the lactose and the corn starch, the mixture is moistened with an aqueous 10% solution of the soluble starch, the moist mass is forced through a 1 mm-mesh screen, the resulting granulate is dried at 40° C, the dry granulate is admixed with the colloidal silicic acid, and the composition is compressed into 200 mgm-tablets in a conventional tablet making machine. Each tablet contains 20 mgm of the benzomorphan and is an oral dosage unit composition with very effective analgesic action.

EXAMPLE 27

Coated pills

The pill core composition is compounded from the following ingredients:

| | |
|---|---|
| (−)-2-(D-Tetrahydrofurfuryl)-[(1R,5R,9R) -2'-hydroxy-5,9-dimethyl-6,7-benzomorphan]methanesulfonate | 15.0 parts |
| Lactose | 100.0 prts |
| Corn starch | 95.0 parts |
| Colloidal silicic acid | 2.0 parts |
| Soluble starch | 5.0 parts |
| Magnesium stearate | 3.0 parts |
| Total | 220.0 parts |

Preparation:

The ingredients are compounded in the same manner as in Example 26, and the composition is compressed into 220 mgm-pill cores which are subsequently coated with a thin shell consisting essentially of a mixture of sugar, talcum and gum arabic and finally polished with beeswax. Each coated pill contains 15 mgm of the benzomorphan compound and is an oral dosage unit composition with very effective analgesic action.

EXAMPLE 28

Suppositories

The suppository composition is compounded from the following ingredients:

| | |
|---|---|
| (−)-2-(L-Tetrahydrofurfuryl)-[(1R,5R,9R) -2'-hydroxy-5,9-dimethyl-6,7-benzomorphan | 10.0 parts |
| Lactose | 150.0 parts |
| Suppository base (e.g. cocoa butter) | 1540.0 parts |
| Total | 1700.0 parts |

Preparation:

The benzomorphan compound is intimately admixed with the lactose, and the mixture is blended with the aid of an immersion homogenizer into the suppository base which had previously been melted and cooled to about 40° C. 1700 mgm-portions of the composition are poured into cooled suppository molds and allowed to harden therein. Each suppository contains 10 mgm of the benzomorphan compound and is a rectal dosage unit composition with very effective analgesic action.

EXAMPLE 29

Hypodermic solution

The solution is compounded from the following ingredients:

| | |
|---|---|
| (−)-2-(L-Tetrahydrofurfuryl)-[(1R,5R,9R) -2'-hydroxy-5,9-dimethyl-6,7-benzomorphan] | 1.0 parts |
| Sodium chloride | 10.0 parts |
| Double-distilled water q.s.ad | 1000.0 parts by vol. |

Preparation:

The benzomorphan compound and the sodium chloride are dissolved in the double-distilled water, the solution is filtered until free from suspended particles, and the filtrate is filled under aseptic conditions into 5 cc-ampules which are subsequently sterilized and sealed. Each ampule contains 1.0 mgm of the benzomorphan compound, and its contents are an injectable dosage unit composition with very effective analgesic action.

EXAMPLE 30

Drop solution

The solution is compounded from the following ingredients:

| | |
|---|---|
| (±)-2-Tetrahydrofurfuryl-2'-hydroxy-5,9α-dimethyl-6,7-benzomorphan (racemic diastereoisomer I) | 0.70 parts |
| Methyl p-hydroxy-benzoate | 0.07 parts |
| Propyl p-hydroxy-benzoate | 0.03 parts |
| De-mineralized water q.s.ad | 100.00 parts by vol. |

Preparation:

The benzomorphan compound and the p-hydroxybenzoates are dissolved in the de-mineralized water, the solution is filtered, and the filtrate is filled into 100 cc-bottles. 10 ml of the solution contain 70 mgm of the benzomorphan compound and are an oral dosage unit composition with very effective analgesic action.

Analogous results are obtained when any one of the other compounds embraced by formula I or a non-toxic, pharmacologically acceptable acid addition salt thereof, is substituted for the particular active ingredient in Examples 26 through 30. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

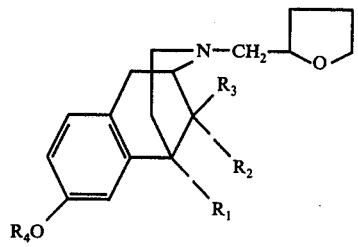

wherein
$R_1$ is methyl, ethyl or propyl,
$R_2$ is hydrogen, methyl or ethyl,
$R_3$ is hydrogen or methyl, and
$R_4$ is hydrogen, alkyl of 1 to 4 carbon atoms or alkanoyl of 2 to 5 carbon atoms, or a non-toxic, pharmacologically acceptable acid addition salt thereof.

2. A racemate, racemic mixture or optically active form of a compound of claim 1.

3. A compound of claim 1, which is one of the formula

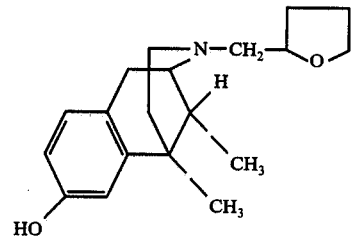

or a non-toxic, pharmacologically acceptable acid addition salt thereof.

4. The compound of claim 1 which is (−)-2-(D-tetrahydrofurfuryl)-[(1R,5R,9R)-2'-hydroxy-5,9-dimethyl-6,7-benzomorphan]methanesulfonate.

5. The racemic diastereoisomer of claim 2, which is a mixture of 2-(D-tetrahydrofurfuryl)-[(1R, 5R, 9R)-2'-hydroxy-5,9-dimethyl-6,7-benzomorphan] and 2-(L-tetrahydrofurfuryl)-[(1S,5S,9S)-2'-hydroxy-5,9-dimethyl-6,7-benzomorphan].

6. The racemic distereoisomer of claim 2, which is a mixture of 2-(L-tetrahydrofurfuryl)-[(1R, 5R, 9R)-2'-hydroxy-5, 9-dimethyl-6, 7-benzomorphan] and 2-(D-tetrahydrofurfuryl)-[(1S, 5S, 9S)-2'-hydroxy- 5, 9-dimethyl-6, 7-benzomorphan].

7. The compound of claim 1 which is (−)-2-(L-tetrahydrofurfuryl)-[(1R,5R,9R)-2'-hydroxy-5,9-dimethyl-6,7-benzomorphan].

8. An analgesic pharmaceutical dosage unit composition consisting essentially of an inert pharmaceutical carrier and an effective analgesic amount of a compound of claim 1.

9. The method of alleviating pain in a warm-blooded animal, which comprises perorally, parenterally or rectally administering to said animal an effective analgesic amount of a compound of claim 1.

* * * * *

UNITED STATES PATENT OFFICE
CERTIFICATE OF CORRECTION

Patent No. 4,087,532          Dated May 2, 1978

Inventor(s) HERBERT MERZ, ADOLF LANGBEIN, GERHARD WALTHER, and KLAUS STOCKHAUS

It is certified that error appears in the above-identified patent and that said Letters Patent are hereby corrected as shown below:

Col. 3, line 44, to the right of the formula insert --(IV)--

Col. 8, lines 51 to 59, the chart should read as follows:

-- L-(+)-tetrahydrofurfuryl alcohol: $[\alpha]_D^{25} = +15.3°$ (c = 5, nitromethane) b.p. 76° C/ 16 mm Hg D-(-)-tetrahydrofurfuryl alcohol: $[\alpha]_D^{25} = -15.7°$ (c = 5, nitromethane) b.p. 76°C/ 16 mm Hg L-(+)-tetrahydrofurfuryl bromide: $[\alpha]_D^{25} = +3.9°$ (c = 5, nitromethane) b.p. 66-67°C/ 16 mm Hg D-(-)-tetrahydrofurfuryl bromide: $[\alpha]_D^{25} = -3.8°$ (c = 5, nitromethane) b.p. 67°C/ 16 mm Hg --

Signed and Sealed this

Seventeenth Day of October 1978

[SEAL]

Attest:

RUTH C. MASON
Attesting Officer

DONALD W. BANNER
Commissioner of Patents and Trademarks